(12) United States Patent
Yamaura

(10) Patent No.: US 8,674,092 B2
(45) Date of Patent: Mar. 18, 2014

(54) TRIALLYL ISOCYANURATE AND PROCESS FOR PRODUCING THE SAME

(75) Inventor: Mabuko Yamaura, Fukushima-ken (JP)

(73) Assignee: Nippon Kasei Chemical Company Limited, Iwaki-shi, Fukushima-ken (JP)

( * ) Notice: Subject to any disclaimer, the term of this patent is extended or adjusted under 35 U.S.C. 154(b) by 0 days.

(21) Appl. No.: 13/287,275

(22) Filed: Nov. 2, 2011

(65) Prior Publication Data
US 2012/0095224 A1   Apr. 19, 2012

Related U.S. Application Data

(63) Continuation-in-part of application No. PCT/JP2010/058566, filed on May 20, 2010.

(30) Foreign Application Priority Data

May 25, 2009 (JP) .................................. 2009-125334

(51) Int. Cl.
*C07D 251/34* (2006.01)
*C07D 251/26* (2006.01)

(52) U.S. Cl.
USPC ............................ 544/221; 544/215; 544/219

(58) Field of Classification Search
USPC ....................................................... 544/221
See application file for complete search history.

(56) References Cited

U.S. PATENT DOCUMENTS

| | | | |
|---|---|---|---|
| 3,322,761 A | 5/1967 | Little | |
| 3,700,667 A | 10/1972 | Hisao et al. | |
| 4,196,289 A | 4/1980 | Saito et al. | |
| 8,198,431 B2 * | 6/2012 | Werle et al. | 540/145 |
| 2009/0312545 A1 | 12/2009 | Werle et al. | |

FOREIGN PATENT DOCUMENTS

| | | |
|---|---|---|
| JP | 47-22588 | 6/1972 |
| JP | 48-26022 | 8/1973 |
| JP | 54-044688 | 4/1979 |
| JP | 11-255753 | 9/1999 |
| WO | WO 2008/006661 | 1/2008 |

OTHER PUBLICATIONS

English language translation of the International Preliminary Report on Patentability and Written Opinion in PCT/JP2010/058566 dated Dec. 22, 2011.
Extended European search report in related European patent application EP 10 78 0473 dated Oct. 8, 2012.
International Search Report for PCT/JP2010/058566, mailed Aug. 10, 2010.

* cited by examiner

*Primary Examiner* — Venkataraman Balasubramanian
(74) *Attorney, Agent, or Firm* — Nixon & Vanderhye P.C.

(57) ABSTRACT

The present invention provides triallyl isocyanurate comprising a less amount of corrosive substances by identifying the corrosive substances among impurities included in the triallyl isocyanurate. Triallyl isocyanurate of the present invention comprises an organic chlorine compound represented by the following chemical formula (I) in an amount of not more than 500 ppm:

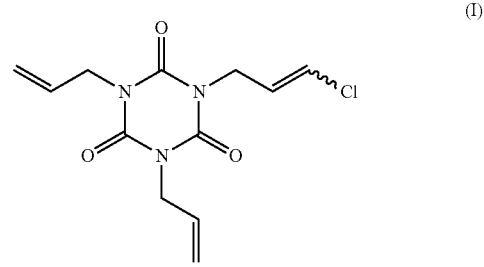

(I)

wherein a bond expressed by a wavy line indicates that the organic chlorine compound is a cis-type compound, a trans-type compound or a mixture comprising the cis-type and trans-type compounds at an optional ratio.

4 Claims, No Drawings

TRIALLYL ISOCYANURATE AND PROCESS FOR PRODUCING THE SAME

This application is a Continuation-In-Part of International Application No. PCT/JP2010/058566 filed May 20, 2010 which designated the U.S. and claims priority to JP Patent Application No. 2009-125334 filed May 25, 2009, the entire contents of each of which are hereby incorporated by reference.

TECHNICAL FIELD

The present invention relates to triallyl isocyanurate and a process for producing the triallyl isocyanurate. The triallyl isocyanurate is hereinafter referred to merely as "TAIC".

BACKGROUND ART

As the method of producing the TAIC, there are known a sodium cyanate method in which allyl chloride and sodium cyanate are reacted to obtain allyl isocyanate, and then the thus obtained allyl isocyanate is subjected to trimerization (Patent Document 1); and an isocyanuric acid method in which allyl chloride and isocyanuric acid (a tautomer of cyanuric acid) are reacted in the presence of a base catalyst (Patent Document 2).

TAIC is useful as a crosslinking agent having excellent heat resistance and chemical resistance, and it is expected to use TAIC in extensive applications such as electronic materials, liquid crystals, semiconductors and solar cells. For example, in printed circuit boards, i.e., plate- or film-shaped members constituting electronic circuits in which a number of electronic parts such as integrated circuits, resistors and capacitors are fixed on a surface thereof, and connected to each other through wirings, there is proposed the method in which TAIC is used as a sealing material for preventing penetration of substances such as liquids and gases into the respective electronic parts (Patent Document 3). In such a proposed method, TAIC is used as a liquid sealing material because the TAIC is present in the form of a viscous liquid (melting point: 26° C.) at an ordinary temperature. In addition, in order to enhance a wettability of TAIC, a silane coupling agent is added thereto. Also, TAIC is used as a crosslinking agent for crosslinkable polymers (Patent Document 4).

Meanwhile, although there is no report for impurities included in TAIC obtained by the above rearrangement of TAC, the impurities which may cause metal corrosion must be removed from TAIC to reduce their content to as small a level as possible.

PRIOR DOCUMENTS

Patent Documents

Patent Document 1: Japanese Patent Publication (KOKOKU) No. 58-35515
Patent Document 2: U.S. Pat. No. 3,065,231
Patent Document 3: Japanese Patent Application Laid-Open (KOKAI) No. 2007-115840
Patent Document 4: Japanese Patent Application Laid-Open (KOKAI) No. 2006-036876

SUMMARY OF THE INVENTION

Problems to be Solved by the Invention

The present invention has been accomplished in view of the above conventional problems. An object of the present invention is to provide TAIC having a less content of corrosive substances by identifying the corrosive substances among impurities included therein.

Means for Solving Problems

As a result of the present inventors' earnest study for achieving the above object, the following knowledges have been attained.

(1) The TAIC obtained by the sodium cyanate method or the isocynauric acid method comprises, as one of impurities, an organic chlorine compound represented by the following chemical formula (I). The organic chlorine compound is gradually hydrolyzed in water to generate chlorine ions which causes corrosion.

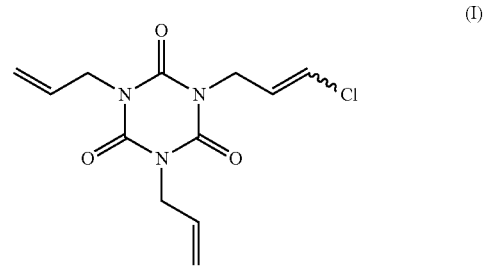 [SMILES: C=CCn1c(=O)n(CC=C)c(=O)n(CC=CCl)c1=O]

(I)

wherein a bond expressed by a wavy line indicates that the organic chlorine compound is a cis-type compound, a trans-type compound or a mixture comprising the cis-type and trans-type compounds at an optional ratio, and this is hereinafter defined in the same way.

(2) The organic chlorine compound represented by the chemical formula (I) is produced by the reaction between sodium cyanate and 1,3-dichloropropene represented by the following chemical formula (II) which is included as impurity in allyl chloride. The organic chlorine compound represented by the chemical formula (I) is also produced by the reaction between cyanuric acid and 1,3-dichloropropene.

(II)

(3) The organic chlorine compound represented by the chemical formula (I) is hardly removed by separation methods such as distillation, whereas the 1,3-dichloropropene represented by the chemical formula (II) can be readily separated from allyl chloride by subjecting the allyl chloride to distillative purification.

The present invention has been attained on the basis of the above findings. In a first aspect of the present invention, there is provided triallyl isocyanurate comprising an organic chlorine compound represented by the following chemical formula (I) in an amount of not more than 500 ppm.

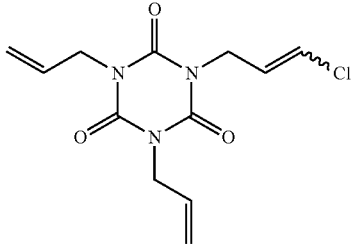

wherein a bond expressed by a wavy line indicates that the organic chlorine compound is a cis-type compound, a trans-type compound or a mixture comprising the cis-type and trans-type compounds at an optional ratio.

In a second aspect of the present invention, there is provided a process for producing triallyl isocyanurate comprising the step of reacting sodium cyanate or isocyanuric acid with ally chloride comprising 1,3-dichloropropene (in the form of a cis-type compound, a trans-type compound or a mixture comprising the cis-type and trans-type compounds at an optional ratio) in an amount of not more than 200 ppm.

Effect of the Invention

The triallyl isocyanurate according to the present invention is free from occurrence of metal corrosion due to impurities included therein, and therefore can be suitably used, for example, as a sealing material for printed circuit boards.

PREFERRED EMBODIMENTS FOR CARRYING OUT THE INVENTION

The present invention is described in detail below.

For the sake of explanation, the process for producing TAIC according to the present invention is first described.

The TAIC according to the present invention may be basically produced by the sodium cyanate method described in the above Patent Document 1 or by the isocyanuric acid method described in the above Patent Document 2.

In the sodium cyanate method, allyl chloride and sodium cyanate are reacted with each other to obtain allyl isocyanate, and then the thus obtained allyl isocyanate is subjected to trimerization. The details of the reaction conditions can be recognized by referring to the above Patent Document 1. In the preferred embodiment of the present invention, allyl chloride is added dropwise into a solution comprising sodium cyanate, calcium chloride, potassium bromide and DMF, and then the resulting reaction mixture is reacted and aged at a temperature of 100 to 150° C. for 0.5 to 5 hr.

In the isocyanuric acid method, allyl chloride and isocyanuric acid are reacted in the presence of a base catalyst. The details of the reaction conditions can be recognized by referring to the above Patent Document 2. In the preferred embodiment of the present invention, allyl chloride is added dropwise into a solution comprising isocyanuric acid, DMF and triethylamine, and then the resulting reaction mixture is reacted and aged at a temperature of 100 to 150° C. for 0.5 to 5 hr.

In the present invention, in any of the above methods, it is important that the allyl chloride used as the raw material has a content of 1,3-dichloropropene (content of a cis-type compound, a trans-type compound or a mixture comprising the cis-type and trans-type compounds at an optional ratio) of not more than 200 ppm.

The industrially used allyl chloride usually comprises impurities such as propyl chloride, 1,2-dichloropropene, 1,3-dichloropropane and 1,3-dichloropropene. Allyl chloride comprising 1,3-dichloropropene in an amount of not more than 200 ppm may be produced by subjecting the industrially used allyl chloride to rectification. The number of theoretical plates in a distillation column used for the rectification is usually not less than 50 plates and preferably 60 to 90 plates. The reflux ratio is usually not less than 5 and preferably 7 to 10. The content of 1,3-dichloropropene (content of a cis-type compound, a trans-type compound or a mixture comprising the cis-type and trans-type compounds at an optional ratio) in the allyl chloride is preferably not more than 100 ppm.

Next, TAIC according to the present invention is described. The TAIC according to the present invention may be produced, for example, by the above-mentioned methods, and is characterized by comprising the organic chlorine compound represented by the following chemical formula (I) in an amount of not more than 500 ppm.

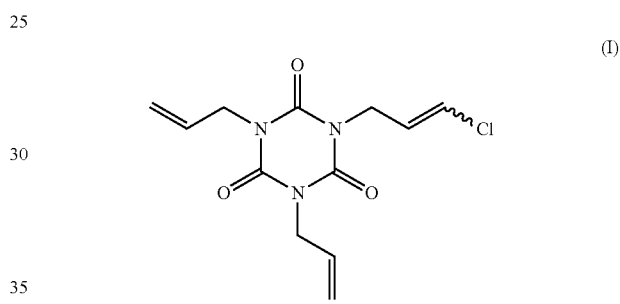

wherein a bond expressed by a wavy line indicates that the organic chlorine compound is a cis-type compound, a trans-type compound or a mixture comprising the cis-type and trans-type compounds at an optional ratio.

The content of the organic chlorine compound represented by the above chemical formula (I) in the TAIC according to the present invention is preferably not more than 300 ppm, more preferably not more than 100 ppm and especially preferably not more than 30 ppm. The TAIC according to the present invention has a less content of impurities which may induce metal corrosion, and therefore can be suitably used as a sealing material for printed circuit boards. In addition, the TAIC according to the present invention may be mixed with a crosslinkable elastomer and then cured by heating or radiation, and the resulting cured product can be used as a sealing material for electronic materials, semiconductors, solar cell materials, etc. Further, the TAIC according to the present invention may also be mixed with a crosslinkable thermoplastic resin and then cured by irradiation with electron beams, etc., and the resulting cured product can be suitably used for coating electric wires, etc.

Meanwhile, as the method of producing the TAIC, in addition to the above sodium cyanate method and isocyanuric acid method, there is also known the production method in which 2,4,6-trichloro-1,3,5-triazine (cyanuric chloride) and allyl alcohol are reacted with each other to obtain triallyl cyanurate (hereinafter referred to merely as "TAC"), and then the thus obtained TAC is subjected to rearrangement reaction (TAC rearrangement method). However, the TAIC obtained by the above rearrangement method comprises no organic chlorine compound represented by the above chemical formula (I).

EXAMPLES

The present invention is described in more detail below by Examples. However, these Examples are only illustrative and not intended to limit the present invention thereto, and various changes or modifications are possible unless they depart from the scope of the present invention. Meanwhile, the analyzing methods used in the following Example and Comparative Example are as follows.

(1) Analysis of 1,3-dichloropropene

The analysis of the 1,3-dichloropropene was carried out by single ion monitoring method (SIM method) using GC-MS (Gas Chromatograph-Mass Spectrometry). The analyzing conditions are shown in Table 1 below. Meanwhile, the detection limit of the measuring device used was 0.5 ppm. In Comparative Example 1, a sample of 1,3-dichloropropene to be analyzed was used in the form of a dilute solution prepared by diluting the 1,3-dichloropropene by 20 times.

TABLE 1

| Device name | "QP-2010" manufactured by Shimadzu Seisakusho Corp. |
| --- | --- |
| Column name | Capillary column "HP-5" (30 m × 0.32 mm; film thickness: 0.25 μm) manufactured by Agilent Inc. |
| Column temperature | 50° C. |
| Injection port temperature | 250° C. |
| Ion source temperature | 230° C. |
| Ion source | EI |
| Pressure | 130 kPa |
| SIM method | m/z 75, 110 |

(2) Analysis of Organic Chlorine Compound of Chemical Formula (I)

The analysis of the organic chlorine compound of the chemical formula (I) was carried out using a gas chromatograph (by an area percentage method). The analyzing conditions are shown in Table 2 below. Meanwhile, a detection limit of the measuring device used was 10 ppm.

TABLE 2

| Device name | "GC-17A" manufactured by Shimadzu Seisakusho Corp. |
| --- | --- |
| Column name | Capillary column "DB-225" (30 m × 0.25 mm; film thickness: 0.25 μm) manufactured by J&W Inc. |
| Column temperature | 150° C. to 220° C. (at a temperature rise rate of 2° C./min) |
| Injection port temperature | 250° C. |
| Detector temperature | 300° C. |
| Pressure | 150 kPa |
| Split ratio | 20 |
| Solvent | Acetone |
| Concentration of sample | 5% by weight |

Comparative Example 1

A solution comprising 100 g of sodium cyanate, 14 g of calcium chloride, 13 g of potassium bromide and 500 g of DMF was maintained at 120° C., and 98 g of allyl chloride (1,3-dichloropropene comprising 140 ppm of a cis isomer and 140 ppm of a trans isomer) were added dropwise to the solution. The resulting reaction solution was reacted and aged, and then subjected to distillation to remove the solvent therefrom, thereby obtaining an oily material. Next, the thus obtained oily material was washed with water, and the obtained organic layer was subjected to distillation under reduced pressure to obtain TAIC in the form of a viscous liquid (yield: 90%). It was confirmed that the thus obtained TAIC comprised the organic chlorine compound represented by the chemical formula (I) in an amount of 590 ppm.

Example 1

The same procedure as defined in Comparative Example 1 was conducted except that allyl chloride comprising 1,3-dichloropropene (comprising 0.1 ppm of a cis isomer and 0.1 ppm of a trans isomer) was used as the raw material, thereby producing TAIC (yield: 91%). As a result, it was confirmed that no organic chloride compound represented by the general formula (I) was detected in the thus obtained TAIC (less than 10 ppm).

Experimental Example 1

Hydrolysis Test of TAIC

A Teflon (registered trademark) pressure container was charged with 1 g of each of the TAICs obtained in the above Example, etc., and 20 g of water, and the contents of the container were heated at 120° C. for 200 hr to measure a chlorine ion concentration in water. The measurement of the chlorine ion concentration in water was carried out using an ion chromatograph (column used: "DIONEX Ion Pack AS12A"; eluent used: 2.7 mM-$Na_2CO_3$/0.3 mM-$NaHCO_3$). The detection limit of the measuring device used was 1 ppm. The results are shown in Table 3.

TABLE 3

| Kind of TAIC | Chlorine ion concentration (ppm) |
| --- | --- |
| Comparative Example 1 | 150 |
| Example 1 | ND (less than 1 ppm) |

What is claimed is:
1. Triallyl isocyanurate comprising an organic chlorine compound represented by the following chemical formula (I) in an amount of not more than 500 ppm:

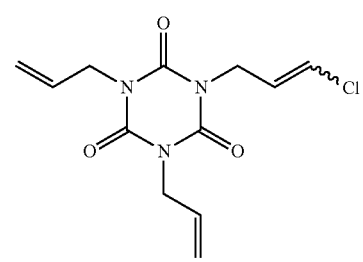

wherein a bond expressed by a wavy line indicates that the organic chlorine compound is a cis-type compound, a trans-type compound or a mixture comprising the cis-type and trans-type compounds at an optional ratio.

2. A process for producing triallyl isocyanurate comprising the steps of reacting allyl chloride with sodium cyanate to obtain allyl isocyanate and subjecting the thus obtained allyl isocyanate to trimerization, wherein the allyl chloride used as a raw material has a content of 1,3-dichloropropene (content of a cis-type compound, a trans-type compound or a mixture comprising the cis-type and trans-type compounds at an optional ratio) of not more than 200 ppm.

3. A process for producing triallyl isocyanurate comprising the step of reacting allyl chloride with isocyanuric acid in the presence of a base catalyst, wherein the allyl chloride used as a raw material has a content of 1,3-dichloropropene (content of a cis-type compound, a trans-type compound or a mixture comprising the cis-type and trans-type compounds at an optional ratio) of not more than 200 ppm.

4. The process according to claim 2, wherein the allyl chloride used as a raw material has a content of 1,3-dichloropropene (content of a cis-type compound, a trans-type compound or a mixture comprising the cis-type and trans-type compounds at an optional ratio) of not more than 100 ppm.

\* \* \* \* \*